United States Patent [19]
Dean et al.

[11] Patent Number: 5,932,572
[45] Date of Patent: *Aug. 3, 1999

[54] TOPICAL ANTI-GLAUCOMA COMPOSITIONS

[75] Inventors: Thomas R. Dean, Weatherford; Louis Desantis, Jr., Forth Worth, both of Tex.

[73] Assignee: Alcon Laboratories, Inc., Fort Worth, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 08/920,314

[22] Filed: Aug. 27, 1997

Related U.S. Application Data

[63] Continuation of application No. 08/526,240, Sep. 11, 1995, abandoned, which is a continuation of application No. 08/115,970, Sep. 1, 1993, abandoned, which is a continuation-in-part of application No. 07/839,869, Feb. 21, 1992, abandoned.

[51] Int. Cl.⁶ .......................... A61K 31/54; A61K 31/535
[52] U.S. Cl. ..................... 514/226.5; 514/235.8; 514/913
[58] Field of Search ............... 514/226.5, 235.8, 514/913

[56] References Cited

U.S. PATENT DOCUMENTS

| | | | |
|---|---|---|---|
| 3,655,663 | 4/1972 | Wasson | 260/247.1 |
| 3,729,469 | 4/1973 | Wasson | 260/247.1 |
| 4,731,368 | 3/1988 | Hoffman, Jr. et al. | 514/301 |
| 4,797,413 | 1/1989 | Baldwin et al. | 514/432 |
| 4,847,289 | 7/1989 | Baldwin et al. | 514/445 |
| 4,863,922 | 9/1989 | Baldwin | 514/232.5 |
| 4,911,920 | 3/1990 | Jani | 424/81 |
| 5,153,192 | 10/1992 | Dean et al. | 514/226.5 |
| 5,240,923 | 8/1993 | Dean et al. | 514/226.5 |

FOREIGN PATENT DOCUMENTS

| | | |
|---|---|---|
| 0 429 732 A1 | 6/1991 | European Pat. Off. |
| 0 452 151 A1 | 10/1991 | European Pat. Off. |
| 0 495 421 A1 | 7/1992 | European Pat. Off. |
| 0 507 224 A2 | 10/1992 | European Pat. Off. |
| 509 752 A2 | 10/1992 | European Pat. Off. |
| 9115486 | 10/1991 | WIPO |
| WO91/02262 | 10/1991 | WIPO |

OTHER PUBLICATIONS

J. Med. Chem., 15:651–655 (1972).
Gunning, F. P., "Medical treatment of glaucoma: developments in research on topical carbonic anhydrase inhibitors," *International Ophthalmology*, 15:11–12 (1991).
Pfeiffer, "Additive Wirkung von Timolol und dem lokalen Karboanhydrasehemmer MK–417 (Sezolamid)," *Fortschr Ophthalmol.*, 88(6):846–847 (1991).
*Annual Reports in Medicinal Chemistry*, 14:81–87 (1979).
J. Med. Chem., 27:503–509 (1984).
J. Med. Chem., 26:7–11 (1983).
J. Med. Chem., 26:1561–1569 (1983).
J. Med. Chem., 26:1109–1112 (1983).
J. Med. Chem., 26:950–957 (1983).
J. Med. Chem., 649–657 (1983).
J. Med. Chem., 26:352–357 (1983).
*Physicians' Desk Reference for Ophthalmology*, 16 Ed., 1988, p. 11.

*Primary Examiner*—Zohreh Fay
*Attorney, Agent, or Firm*—Sally Yeager

[57] ABSTRACT

Ophthalmic pharmaceutical compositions useful in controlling elevated intraocular pressure associated with glaucoma and ocular hypertension are described. The compositions comprise a combination of a beta-blocker and a carbonic anhydrase inhibitor to reduce the production of aqueous humor, preferably formulated as a suspension having a pH between about 6.8 and about 7.8. These compositions may additionally contain a mucomimetic anionic polymer and/or a finely-divided drug carrier substrate to provide sustained release. A method of controlling elevated intraocular pressure with these compositions is also described.

23 Claims, No Drawings

TOPICAL ANTI-GLAUCOMA COMPOSITIONS

This application is a Continuation; application under 37 CFR 1.62 of prior application Ser. No. 08/526,240, filed on Sep. 11, 1995 now abandoned, which is a continuation of Ser. No. 08/115,970, filed Sep. 1, 1993 now abandoned, which is a continuation-in-part of Ser. No. 07/839,869, filed Feb. 21, 1992 now abandoned.

BACKGROUND OF THE INVENTION

The present invention relates to the field of ophthalmology. In particular, the invention relates to the treatment of glaucoma and associated elevations of intraocular pressure and to the treatment of ocular hypertension associated with other diseases or conditions.

Although the underlying causes of glaucoma are not understood, its symptoms often include elevated intraocular pressure, which may be caused either by over-production or inadequate outflow of aqueous humor. If left untreated, or if inadequately treated, glaucoma can lead to blindness or significant loss of vision. There is therefore a continuing need for therapies which control the elevated intraocular pressure associated with glaucoma.

There are currently a number of drugs utilized in the treatment of glaucoma, including: miotics (e.g., pilocarpine, carbachol and acetylcholinesterase inhibitors); sympathomimetics (e.g., epinephrine, dipivalylepinephrine and parn-amino clonidine); beta-blockers (e.g., betaxolol, levobunolol and timolol); and carbonic anhydrase inhibitors (e.g., acetazolamide, methazolamide and ethoxzolamide). Miotics and sympathomimetics are believed to lower intraocular pressure ("IOP") by increasing the outflow of aqueous humor, while beta-blockers and carbonic anhydrase inhibitors are believed to lower IOP by decreasing the formation of aqueous humor. All four types of drugs have potentially serious side effects. Miotics such as pilocarpine can cause blurring of vision and other visual side effects, which may lead either to decreased patient compliance or to termination of therapy. Carbonic anhydrase inhibitors can also cause serious side effects which affect patient compliance and/or necessitate the withdrawal of treatment. Moreover, at least one beta-blocker, timolol, has increasingly become associated with serious pulmonary side effects attributable to its effect on beta-2 receptors in pulmonary tissue.

A significant number of glaucoma patients require the administration of more than one type of drug in order to achieve therapeutic control over their IOP. That is, a single drug does not provide adequate control of IOP in these patients. Treatment which includes the use of two or more of the above-cited classes of drugs requires the patient to apply the compositions to the affected eye(s) in separate, spaced dosages several times a day. Patient compliance with such complicated dosage regimens can be very poor, particularly with elderly patients. Since the majority of glaucoma patients are elderly, this is a significant problem.

In light of the foregoing circumstances, it is clear that a need exists for new, more potent anti-glaucoma compositions which avoid or reduce the above-cited side effects, while increasing patient compliance. The present invention is directed to such compositions.

SUMMARY OF THE INVENTION

As mentioned above, two or more different types of drugs are sometimes required to achieve therapeutic control of intraocular pressure. The use of a combination of drugs from two of the above-mentioned four classes of drugs has the advantage of reducing intraocular pressure via two different mechanisms. In particular, although both beta-blockers and carbonic anhydrase inhibitors are believed to lower IOP by decreasing the formation of aqueous humor, each of these classes of drugs operates by different mechanisms; therefore, a combination of at least one beta-blocker and at least one carbonic anhydrase inhibitor ("CAI"), when formulated in a composition also including anionic mucomimetic polymers and finely-divided drug carrier substrates ("DCS"—defined below) provides reduction of IOP and additionally provides comfortable, sustained-released compositions.

It has also been found, quite unexpectedly, that certain CAI's which have exceptionally low inherent aqueous solubility are effective in lowering and controlling IOP when dosed topically to the eye as suspensions, preferably having neutral pH. These formulations have been found to be very well tolerated, and appear to be significantly more comfortable and have fewer side effects than solutions of CAI's which have higher inherent aqueous solubility (these solutions are typically formulated at a pH between about 5.0 and 6.0). As such, combinations of beta-blockers with these low aqueous solubility CAI's formulated as suspensions will provide comfortable and effective medicaments for lowering and controlling IOP. The additional inclusion of anionic mucomimetic polymers and/or DCS will provide sustained release formulations.

Thus, the present invention is directed to such anti-glaucoma compositions, as well as methods of controlling IOP utilizing these compositions.

DETAILED DESCRIPTION OF THE INVENTION

The anti-glaucoma compositions of the present invention comprise a combination of one or more beta-blockers and one or more carbonic anhydrase inhibitors, formulated as suspensions having a pH between about 5.0 and about 7.8, preferably formulated as suspensions having a pH between about 6.8 and about 7.8. The anti-glaucoma compositions of the present invention may additionally contain anionic mucomimetic polymers and/or DCS to provide sustained release.

The beta-blockers which are useful in the compositions of the present invention include all beta-blockers which demonstrate the requisite cation charge and intraocular pressure effect. Such beta-blockers are typically represented by the following generic structure:

$$R'_1\text{—}O\text{—}CH_2\text{—}CH(OH)\text{—}CH_2\text{—}NR'_2R'_3 \qquad (I)$$

wherein:
  $R'_1$, is a substituted or unsubstituted cyclic or aliphatic moiety; cyclic moieties include mono- and polycyclic structures which may contain one or more heteroatoms selected from C, N, and O; and
  $R'_2$ and $R'_3$ are independently selected from H and substituted and unsubstituted alkyl.

With regard to Structure (I), above, the following references are hereby incorporated by reference herein: *Annual Reports in Medicinal Chemistry.* 14:81–87 (1979); *J. Med. Chem.,* 26:1570–1576 (1983); ibid., 27:503–509 (1984); ibid. 26:7–11 to (1983); ibid., 26:1561–1569 (1983); ibid., 26:1109–1112 (1983); ibid., 26:950–957 (1983); ibid., 26:649–657; and ibid., 26:352–357 (1983). Representative beta-blockers include the racemic and enantiomeric forms of: betaxolol, timolol, metoprolol, befunolol, falintolol, levobunolol, carteolol, mepindolol, pindolol, bisoprolol, bopindolol, atenolol, arotinolol, acebutolol, nadolol, celiprolol, metipranolol, bevantolol, ICI 118,551, pamatolol, penbutolol, toliprolol, tiprenolol, practolol, procinolol, exaprolol, ciclprolol, carazolol, tazolol, tienoxolol, oxprenolol, propranolol, IPS 339, labetolol, dilevalol, esmolol, bupranolol, bunolol, isoxaprolol, diacetolol, hydroxylevobunolol, carvedilol and the like. The preferred beta-blocker is betaxolol, especially S-betaxolol.

Other preferred beta-blockers are certain 4-(3-substituted amino-2-hydroxypropoxy)-1,2,5-thiadiazoles which were originally disclosed in German Patent No. 1,925,956 (issued in 1969 to B. K Wasson), equivalent to U.S. Pat. No. 3,655,663 (issued in 1972) and U.S. Pat. No. 3,729,469 (issued in 1973). These thiadiazoles have the following general structure:

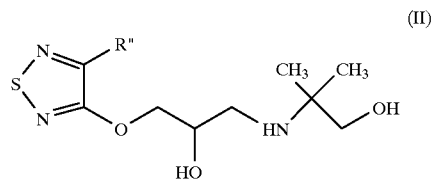

and optically active isomers and pharmacologically acceptable salts thereof, wherein R" represents: (1) hydrogen; (2) halogen, preferably chloro or bromo; (3) $C_{1-5}$ lower alkyl having either a straight or branched chain such as methyl, ethyl, propyl, isopropyl, butyl iso-, secondary- or tert-butyl and amyl, including all of its branched chain configurations; (4) $C_{2-5}$ lower alkenyl, such as vinyl, allyl, methallyl and the like; (5) a group having the structure Y-X-Z-, wherein Y is either a straight or branched chain $C_{1-4}$ alkyl optionally substituted with a phenyl group or a phenyl optionally substituted with one or more halogen atoms (especially chloro, bromo, fluoro), hydroxy, $C_{1-3}$ lower alkyl or alkoxy, X is oxygen or sulfur and Z is a $C_{1-2}$ alkyl; (6) a carbamoyl group having the structure R"$_1$HNCO, wherein R"$_1$ is a $C_{1-5}$ lower alkyl; (7) $C_{1-5}$ cycloalkyl, such as cyclopropyl, cyclobutyl, cyclopentyl, cyclohexyl and the like; (8) $C_{1-4}$ lower alkoxy, either a straight or branched chain and including methoxy, ethoxy, propoxy, isopropoxy, butoxy, and pentoxy (the latter groups existing in either straight or branched configuration); (9) phenyl or substituted phenyl, wherein the substitutes are selected from one or more halogen atoms (preferably chloro or fluoro) and a $C_{1-3}$ is lower alkyl or alkoxy; (10) phenyl-lower alkyl, wherein the lower alkyl moiety is either a straight or branched chain and has from 1 to 4 carbons and the phenyl moiety can be unsubstituted or substituted with one or more halogen atoms (preferably chloro, fluoro, or bromo) or $C_{1-3}$ lower alkyl or alkoxy; (11) an amino having the structure—NR"$_2$R"$_3$, wherein R"$_2$ represents hydrogen, $C_{1-4}$ lower alkyl and $C_{2-4}$ hydroxy-substitited substituted lower alkyl, R"$_3$ represents hydrogen, $C_{1-4}$ lower alkyl, a hydroxy-substituted lower alkyl and phenyl, or R"$_2$ and R"$_3$ can be joined together either directly to give a 3 to 7 membered ring with the nitrogen to which they are attached thereby forming aziridinyl, azetidinyl, pyrrolidyl, piperidyl, or a hexahydroazepinyl group, said 3 to 7 membered rings being either unsubstituted or substituted, preferably with one or more $C_{1-5}$ lower alkyl and $C_{1-3}$ hydroxy-lower alkyl, or alternatively R"$_2$ and R"$_3$ can be joined through an oxygen, nitrogen or sulfur atom to form a 5 or 6 membered ring, advantageously a morpholino, hexahydropyrimidyl, thiazolidinyl, p-thiaiinyl, piperazinyl and the like group optionally substituted by $C_{1-3}$ lower alkyl; or (12) R additionally can be a 5 or 6 membered heterocyclic ring having oxygen, nitrogen or sulfur as the hetero atom and preferably the 2-furyl, 2- or 3-thienyl, 2-pyrryl and the o-, m- or p-pyridyl. These thiadiazoles may be prepared by the methods disclosed in U.S. Pat. No. 3,655,663 and U.S. Pat. No. 3,729,469 whose entire contents are incorporated by reference herein. Especially preferred thiadiazoles are those of Structure (II), above, wherein R" is chloro, ethyl, allyl, cyclopropyl, ethoxy, phenyl, phenyl-chloromethyl, or 2-(cyclopropylmethoxy)ethyl.

The CAIs which are useful in the compositions of the present invention include all thiophene sulfonamides and thienothiazines which lower and control IOP by inhibiting carbonic anhydrase when administered topically. Representative CAIs are disclosed in: U.S. Pat. Nos. 4,797,413 (Baldwin et al.), 4,847,289 (Baldwin et al.) and 4,731,368 (Hoffman Jr., et al.); U.S. Pat. No. 5,153,192 (Dean et al.) and U.S. patent application Ser. No. 07/775,313 (filed Oct. 9, 1991); PCT/US91/02262 (filed Apr. 9, 1990); and EP 452 151 (published Oct. 16, 1991). The entire contents of each of the above-mentioned patents and patent applications are hereby incorporated by reference herein.

Preferred CAIs of the present invention are those disclosed in U.S. patent application Ser. No. 07/775,313. Such CAIs have the following generic structure:

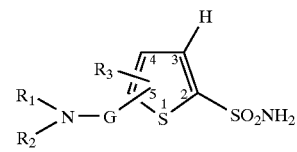

or a pharmaceutically acceptable salt thereof, wherein:

$R_1$ is: H; $C_{1-4}$ alkyl; $C_{2-4}$ alkyl substituted optionally with OH, halogen, $C_{1-4}$ alkoxy or C(=O)R$_7$;

$R_2$ is: H; $C_{1-8}$ alkyl; $C_{2-8}$ alkyl substituted with OH, NR$_5$R$_6$, halogen, $C_{1-4}$ alkoxy, $C_{2-4}$alkoxyC$_{1-4}$alkoxy, OC(=O)R$_7$, or C(=O)R$_7$; $C_{3-7}$ alkenyl unsubstituted or substituted optionally with OH, NR$_5$R$_6$, or $C_{1-4}$ alkoxy; $C_{3-7}$ alkynyl unsubstituted or substituted optionally with OH, NR$_5$R$_6$, or $C_{1-4}$ alkoxy, $C_{1-3}$ alkyl substituted with phenyl or R$_{10}$ either of which can be unsubstituted or substituted optionally with $C_{1-3}$ alkyl, $C_{1-3}$ haloalkyl, OH, (CH$_2$)$_n$NR$_5$R$_6$, halogen, $C_{1-4}$ alkoxy, $C_{1-4}$ haloalkoxy, C(=O)R$_7$, S(=O)$_m$R$_8$ or SO$_2$NR$_5$R$_6$, wherein m is 0–2 and n is 0–2; $C_{1-4}$ alkoxy substituted optionally with NR$_5$R$_6$, halogen, $C_{1-4}$ alkoxy, or C(=O)R$_7$; phenyl or R$_{10}$ either of which can be unsubstituted or substituted optionally with $C_{1-3}$ alkyl, $C_{1-3}$ haloalkyl, OH, (CH$_2$)$_n$NR$_5$R$_6$, halogen, $C_{1-4}$ alkoxy, $C_{1-4}$ haloalkoxy, C(=O)R$_7$, S(=O)$_m$R$_8$ or SO$_2$NR$_5$R$_6$, wherein m is 0–2 and n is 0–2; provided that $R_1$ and $R_2$ cannot both be H; or $R_1$ and $R_2$ can be joined to form a saturated ring of 5 or 6 atoms selected from O, S, C or N, such as, pyrrolidine, oxazolidine, thiomorpholine, thiomorpholine 1,1 dioxide, morpholine, piperazine, thiazolidine 1,1 dioxide, or tetrahydrooxazine, which can be unsubstituted or substituted optionally on carbon with OH, NR$_5$R$_6$, halogen, $C_{1-4}$ alkoxy, C(=O)R$_7$, $C_{1-6}$ alkyl, $C_{1-6}$ alkyl substituted optionally with OH, NR$_5$R$_6$, halogen, $C_{1-4}$ alkoxy, C(=O)R$_7$ or on nitrogen with NR$_5$R$_6$, $C_{1-4}$ alkoxy, C(=O)R$_7$, $C_{1-6}$ alkyl or $C_{2-6}$ alkyl substituted optionally with OH, NR$_5$R$_6$, halogen, $C_{1-4}$ alkoxy or C(=O)R$_7$;

R$_3$ is: H; halogen; C$_{1-4}$ alkyl; C$_{1-8}$ alkoxy; C$_{1-8}$ alkylthiol; C$_{2-8}$ alkoxy substituted optionally with OH, NR$_5$R$_6$, halogen, C$_{1-4}$ alkoxy or C(=O)R$_7$; C$_{1-4}$ alkyl substituted optionally with R$_4$; or R$_1$ and R$_3$ can be joined together with carbon atoms to form a ring of from 5 to 7 members in which said carbon atoms can be unsubstituted or substituted optionally with R$_4$;

R$_4$ is: OH; C$_{1-4}$ alkyl unsubstituted or substituted optionally with OH, NR$_5$R$_6$, halogen, C$_{1-4}$ alkoxy or C(=O)R$_7$; C$_{1-4}$ alkoxy; C$_{2-4}$alkoxy substituted optionally with OH, NR$_5$R$_6$, halogen, C$_{1-4}$ alkoxy or C(=O)R$_7$; NR$_5$R$_6$; phenyl or R$_{10}$ either of which can be unsubstituted or substituted optionally with OH, (CH$_2$)$_n$NR$_5$R$_6$, halogen, C$_{1-4}$ alkoxy, C$_{1-4}$ haloalkoxy, C(=O)R$_7$, S(=O)$_m$R$_8$ or SO$_2$NR$_5$R$_6$, wherein m is 0–2 and n is 0–2;

Provided that when G is SO$_2$ and R$_3$ is in the 4 position and is H or halogen then R$_1$ and R$_2$ are not H. C$_{1-6}$ alkyl substituted optionally with OH, C$_{1-6}$alkoxy, C$_{2-6}$ alkoxycarbonyl, C$_{2-6}$ alkenyl, phenyl, phenoxy, pyridyl, tetrahydrofuryl, C$_{2-6}$ alkanoyl, C$_{2-6}$ alkenyl, nor are they joined to form a 5, 6 or 7 member ring, saturated or unsaturated, comprised of atoms selected optionally from C, O, S, N in which said nitrogen, when saturated, is substituted optionally with H or C$_{1-4}$ alkyl or in which said carbon is substituted optionally with C$_{1-6}$ alkyl, C$_{1-6}$ alkoxy or OH; and when R$_3$ is in the 5 position and is H, Cl, Br, or C$_{1-3}$ alkyl then neither R$_1$ nor R$_2$ can be H or C$_{1-4}$ alkyl; and when G is C(=O) and in the 5- position and R$_3$ is H, then R$_1$ and R$_2$ cannot both be CH$_3$;

R$_5$ R$_6$ are the same or different and are: H; C$_{1-4}$ alkyl; C,, alkyl substituted optionally with OH, halogen, C$_{1-4}$ alkoxy or C(=O)R$_7$; C$_{1-4}$ alkoxy; C$_{2-4}$ alkoxy substituted optionally with OH, halogen, C$_{1-4}$ alkoxy or C(=O)R$_7$; C$_{3-7}$alkenyl unsubstituted or substituted optionally with OH, NR$_5$R$_6$ or C$_{1-4}$ alkoxy; C$_{3-7}$ alkynyl unsubstituted or substituted optionally with OH, NR$_5$R$_6$, or C$_{1-4}$ alkoxy; C$_{1-2}$alkyl-C$_{3-5}$cycloakl; C(=O)R$_7$ or R$_5$ and R6 can be joined to form a ring of 5 or 6 atoms selected from O, S, C or N, such as, pyrrolidine, oxazolidine, thiomorpholine, thiomorpholine 1,1 dioxide, morpholine, piperazine or thiazolidine 1,1-dioxide, which can be unsubstituted or substituted optionally on carbon with OH, (=O), halogen, C$_{1-4}$ alkoxy, C(=O)R$_7$, C$_{1-6}$ alkyl, C$_{1-6}$ alkyl substituted optionally with OH, halogen, C$_{1-4}$ alkoxy, C(=O)R$_7$ or on nitrogen with C$_{1-4}$alkoxy, C(=O)R$_7$, S(=O)$_m$R$_8$, C$_{1-6}$ alkyl or C$_{2-6}$ alkyl substituted optionally with OH, halogen, C$_{1-4}$alkoxy, C(=O)R$_7$ or on sulfur by (=O)$_m$, wherein m is 0–2;

R$_7$ is: C$_{1-8}$ alkyl; C$_{1-4}$, alkyl substituted optionally with OH NR$_5$R$_6$, halogen, C$_{1-4}$ alkoxy or C(=O)R$_9$; C$_{1-4}$ alkoxy; C$_{2-4}$ alkoxy substituted optionally with OH, NR$_5$R$_6$, halogen or C$_{1-4}$alkoxy; NR$_5$R$_6$; or phenyl or R$_{10}$ either of which can be unsubstituted or substituted optionally with OH, halogen, C$_{1-3}$ alkyl, C$_{1-3}$ haloalkoxy, (CH$_2$)$_n$NR$_5$R$_6$, S(=O)$_m$R$_8$ or SO$_2$NR$_5$R$_6$, wherein n is 0 or 1 and m is 0–2;

R$_8$ is: C$_{1-4}$ alkyl; C$_{2-4}$alkyl substituted optionally with OH, NR$_5$R$_6$, halogen, C$_{1-4}$ alkoxy or C(=O)R$_7$;

R$_9$ is: C$_{1-4}$ alkyl; C$_{1-4}$ alkoxy; amino, C$_{1-3}$ alkylamino, or di-C$_{1-3}$ alkylamino;

R$_{10}$ is: a monocyclic ring system of 5 or 6 atoms composed of C, N, O, and/or S, such as furan, thiophene, pyrrole, pyrazole, imidazole, triazole, tetrazole, oxazole, isoxazole, isothiazole, thiazole, thiadiazole, pyridine, pyrimidine, pyridazine, and pyrazine; and G is: C(=O) or SO$_2$.

In the above definitions, the total number of carbon atoms in a substituent group is indicated by the C$_{i-j}$ prefix where i and j are numbers from 1 to 8 for example. This C$_{i-j}$ definition includes both the straight and branched chain isomers. For example, C$_{1-4}$ alkyl would designate methyl through the butyl isomers; and C$_{1-4}$ alkoxy would designate methoxy through the butoxy isomers.

The term "halogen," either alone or in compound words such as "haloalkyl," means fluorine, chlorine, bromine or iodine. Further, when used in compound words such as "haloalkyl," said alkyl may be partially or fully substituted with halogen atoms, which may be the same or different.

Structure (III) includes isomers, wherein R$_3$ and GNR$_1$R$_2$ are attached to the 4 and 5 position respectively or R$_3$ is attached to the 5 position and GNR$_1$R$_2$ is attached to the 4 position. Many of the novel compounds of Structure (III) possess one or more chiral centers and this invention includes all enantiomers, diastereomers and mixtures thereof.

Especially preferred CAIs of the present invention are those listed in Table 1, below.

TABLE 1

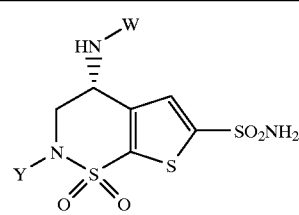

| | W | Y | CHEMICAL NAME |
|---|---|---|---|
| 1 | CH$_2$CH$_3$ | (CH$_2$)$_2$OCH$_2$CH$_3$ | (R)-3,4-Dihydro-2-(2-ethoxy)ethyl-4-ethylamino-2H-thieno[3,2-e]-1,2-thiazine-6-sulfonamide 1,1-dioxide hydrochloride |
| 2 | (CH$_2$)$_2$CH$_3$ | (CH$_2$)$_2$OCH$_2$CH$_3$ | (R)-3,4-Dihydro-2-(2-ethoxy)ethyl-4-propylamino-2H-thieno[3,2-e]-1,2-thiazine-6-sulfonamide 1,1-dioxide hydrochloride |
| 3 | CH$_2$CH$_3$ | (CH$_2$)$_3$OCH$_3$ | (R)-3,4-Dihydro-4-ethylamino-2-(3-methoxy)propyl-2H-thieno[3,2-e]-1,2-thiazine-6-sulfonamide 1,1-dioxide hydrochloride |

TABLE 1-continued

[Structure: thieno[3,2-e]-1,2-thiazine-6-sulfonamide 1,1-dioxide core with HN-W at position 4 and Y on ring nitrogen]

| | W | Y | CHEMICAL NAME |
|---|---|---|---|
| 4 | $(CH_2)_2CH_3$ | $(CH_2)_3CH_3$ | (R)-3,4-Dihydro-2-(3-methoxy)propyl-4-propylamino-2H-thieno[3,2-e]-1,2-thiazine-6-sulfonamide 1,1-dioxide hydrochloride |
| 5 | $CH_2CH_3$ | $(CH_2)_2O(CH_2)_2OCH_3$ | (R)-3,4-Dihydro-4-ethylamino-2-[2-methoxyethoxy)ethyl]-2H-thieno[3,2-e]-1,2-thiazine-6-sulfonamide 1,1-dioxide hydrochloride |
| 6 | $(CH_2)_2CH_3$ | $(CH_2)_2O(CH_2)_2OCH_3$ | (R)-3,4-Dihydro-2-[2-methoxyethoxy)ethyl]-4-propylamino-2H-thieno[3,2-e]-1,2-thiazine-6-sulfonamide 1,1-dioxide hydrochloride |
| 7 | $CH_2CH_3$ | $(CH_2)_3O(CH_2)_2OCH_3$ | (R)-3,4-Dihydro-4-ethylamino-2-[3-(2-methoxy)ethoxy]propyl-2H-thieno[3,2-e]-1,2-thiazine-6-sulfonamide 1,1-dioxide hydrochloride |
| 8 | $(CH_2)_2CH_3$ | $(CH_2)_3O(CH_2)_2OCH_3$ | (R)-3,4-Dihydro-2-[3-(methoxyethoxy)propyl]-4-propylamino-2H-thieno[3,2-e]-1,2-thiazine-6-sulfonamide 1,1-dioxide hydrochloride |
| 9 | $CH_2CH_3$ | $(CH_2)_2OCH_3$ | (R)-3,4-Dihydro-4-ethylamino-2-(2-methoxy)ethyl-2H-thieno[3,2-e]-1,2-thiazine-6-sulfonamide 1,1-dioxide hydrochloride |
| 10 | $(CH_2)_2CH_3$ | $(CH_2)_2OCH_3$ | (R)-3,4-Dihydro-2-(2-methoxy)ethyl-4-propylamino-2H-thieno[3,2-e]-1,2-thiazine-6-sulfonamide 1,1-dioxide hydrochloride |
| 11 | $CH_2CH_3$ | $CH_3$ | (R)-3,4-Dihydro-4-ethylamino-2-methyl-2H-thieno[3,2-e]-1,2-thiazine-6-sulfonamide 1,1-dioxide hydrochloride |
| 12 | $CH_2CH_3$ | $(CH_2)_4OCH_3$ | (R)-4-ethylamino-3,4-dihydro-2-(4-methoxy)butyl-2H-thieno[3,2-e]-1,2-thiazine-6-sulfonamide 1,1-dioxide |
| 13 | $(CH_2)_2CH_3$ | $(CH_2)_4OCH_3$ | (R)-3,4-dihydro-2-(4-methoxy)butyl-4-propylamino-2-thieno[3,2-e]-1,2-thiazine-6-sulfonamide 1,1-dioxide |
| 14 | $CH_2CH_3$ | 4-$OCH_3$—Ph | (R)-4-Ethylamino-2-(4-methoxyphenyl)-3,4-dihydro-2H-thieno[3,2-e]-1,2-thiazine-6-sulfonamide 1,1-dioxide hydrochloride |
| 15 | $CH_2CH_3$ | 3-$OCH_3$—Ph | (R)-4-Ethylamino-3,4-dihydro-2-(3-methoxyphenyl)-2H-thieno[3,2-e]-1,2-thiazine-6-sulfonamide 1,1-dioxide hydrochloride |
| 16 | $CH_2CH_3$ | 4-OH—Ph | (R)-4-Ethylamino-2-(4-hydroxyphenyl)-3,4-dihydro-2H-thieno[3,2-e]-1,2-thiazine-6-sulfonamide 1,1-dioxide hydrochloride |
| 17 | $CH_2CH_3$ | 3-OH—Ph | (R)-4-Ethylamino-3,4-dihydro-2-(3-hydroxyphenyl)-2H-thieno[3,2-e]-1,2-thiazine-6-sulfonamide 1,1-dioxide hydrochloride |
| 18 | $CH_2CH_3$ | $CH_2$-(3-OH—Ph) | (R)-4-Ethylamino-3,4-dihydro-2-(3-hydroxyphenylmethyl)-2H-thieno[3,2-e]-1,2-thiazine-6-sulfonamide 1,1-dioxide hydrochloride |
| 19 | $CH_2CH_3$ | $CH_2$-(3-$OCH_3$—Ph) | (R)-4-Ethylamino-3,4-dihydro-2-(3-methoxyphenylmethyl)-2H-thieno[3,2-e]-1,2-thiazine-6-sulfonamide 1,1-dioxide hydrochloride |
| 20 | $CH_2CH_3$ | $CH_2CH(CH_3)_2$ | (R)-4-Ethylamino-3,4-dihydro-2-(2-methylpropyl)-2H-thieno[3,2-e]-1,2-thiazine-6-sulfonamide 1,1-dioxide hydrochloride |
| 21 | $CH_2CH_3$ | $(CH_2)_6OH$ | (R)-4-Ethylamino-3,4-dihydro-2-(6-hydroxyhexyl)-2H-thieno[3,2-e]-1,2-thiazine-6-sulfonamide 1,1-dioxide hydrochloride |
| 22 | $CH_2CH(CH_3)_2$ | $(CH_2)_3OH$ | (R)-3,4-Dihydro-2-(3-hydroxypropyl)-4-(2-methylpropyl)amino-2H-thieno[3,2-e]-1,2-thiazine-6-sulfonamide 1,1-dioxide hydrochloride hemihydrate |
| 23 | [Structure: HN—$(CH_2)_2CH_3$ on thieno[2,3-b]thiopyran ring with $CH_3O(CH_2)_3$— substituent and $SO_2NH_2$] | | (−)-trans-5,6-dihydro-6-(3-methoxy)propyl-4-propylamino-4H-thieno-[2,3-b]thiopyran-2-sulfonamide 7,7-dioxide |

In general, an amount of a beta-blocker less than or equal to about 2.0% by weight (wt %) and amount of a CAI less than or equal to about 5 wt % are used. It is preferred that an amount of beta-blocker between about 0.01 and about 1.0 wt % is used and it is especially preferred to use an amount between about 0.05 to about 0.5 An amount of a CAI between about 0.25 and about 3 wt % is preferred and an wt %. amount between about 0.5 and about 2 wt % is especially preferred. The ratio by weight of beta-blocker to CAI is generally between about 4:1 to about 1:300, preferably between about 1:1 to about 1:40.

The high molecular weight, anionic mucomimetic polymers useful in the present invention have a molecular weight between about 50,000 and 6 million daltons. The polymers are characterized as having carboxylic acid functional groups and preferably contain between 2 and 7 carbon atoms per functional group. The gels which form during preparation of the ophthalmic polymer dispersion have a viscosity between about 1,000 to about 300,000 centipoise (cps). Suitable polymers are carboxy vinyl polymers, preferably those called Carbomers, e.g., Carbopol® (B. F. Goodrich Co., Cleveland, Ohio). Specifically preferred are Carbopol® 934 and 940. Such polymers will typically be employed in an amount between about 0.05 and about 8.0 wt %, depending on the desired viscosity of the composition. Pourable liquid compositions generally comprise an amount of the polymer between about 0.05 and about 2.0 wt %.

The DCS component of the present compositions is added to provide an additional means of controlling release, as well as to prevent the stinging which often occurs with the topical administration of certain drugs, such as betaxolol. As used herein, the term "finely-divided drug carrier substrate" (or "DCS") means finely-divided solids, colloidal particles, or soluble polymers and/or polyelectrolytes which are capable of selective adsorption or binding with drug molecules. Examples of DCS include, but are not limited to: finely divided silica, such as fumed silica, silicates and bentonites; ion exchange resins, which can be anionic, cationic or non-ionic in nature; and soluble polymers, such as, alginic acid, pectin, soluble carrageenans, Carbopol®, and polystyrene sulfonic acid. Preferred DCS are the ion exchange resins. Some resins which are used in chromatography make ideal DCS for binding drugs in the compositions of the present invention. The DCS component is present in the compositions of the present invention at a concentration between about 0.05 and about 10.0% by weight.

The size of the DCS can be important, both with respect to mode of action and comfort. The average particle size of the typical commercially available form of the DCS material of choice, an ion exchange resin, is about 40 to about 150 microns. Such particles are most conveniently reduced to a particle size range of about 1.0 to about 25.0 microns, preferably between about 1.0 and 10.0 microns, by ball milling, according to known techniques. In the alternative, small particles may be synthesized in the optimal size range of 3–7 microns. Although this procedure can be more expensive, it is superior in providing a more uniform and narrow distribution of sizes in the preferred range.

These anionic mucomimetic polymers and DCS are discussed in greater detail in U.S. Pat. No. 4,911,920 issued Mar. 27, 1990 and EP. 507 224 (published Oct. 7, 1992).

The entire contents of the patent and patent application are hereby incorporated by reference herein.

In addition to the above-described principal ingredients, the anti-glaucoma compositions of the present invention may further comprise various formulatory ingredients, such as antimicrobial preservatives and tonicity agents. Examples of suitable antimicrobial preservatives include: benzalkonium chloride, thimerosal, chlorobutanol, methyl paraben, propyl paraben, phenylethyl alcohol, edetate disodium, sorbic acid, Onamer M® and other agents equally well-known to those skilled in the art. Such preservatives, if utilized, will typically be employed in an amount between about 0.001 to 1.0 wt %. Examples of suitable agents which may be utilized to adjust the tonicity or osmolality of the formulations include: sodium chloride, potassium chloride, mannitol, dextrose, glycerin and propylene glycol. Such agents, if utilized, will typically be employed in an amount between about 0.1 to 10.0 wt %.

As will be appreciated by those skilled in the art, the compositions may be formulated in various dosage forms suitable for topical ophthalmic delivery, including solutions, suspensions, emulsions, gels and erodible solid ocular inserts. The compositions preferably are aqueous, have a pH between 5.0 to 7.8 and an osmolality between 280 to 320 milliOsmoles per kilogram (mOsm/kg).

The following example further illustrates the anti-glaucoma compositions of the present invention.

EXAMPLE 1

The following formulations are typical of aqueous ophthalmic suspensions of the present invention.

| | AMOUNT (wt %) | | | | | |
|---|---|---|---|---|---|---|
| INGREDIENT | A | B | C | D | E | F |
| Betaxolol HCl | 0.28 | — | 0.28 | — | 0.28 | — |
| Compound 3* | 1.7** | 1.7** | — | — | — | — |
| Compound 12* | — | — | 1.5 | 1.5 | — | — |
| Compound 13* | — | — | — | — | 1.5 | 1.5 |
| Timolol maleate | — | 0.68 | — | 0.68 | — | 0.68 |
| BAC | 0.01 | 0.01 | 0.01 | 0.01 | 0.01 | 0.01 |
| EDTA | 0.05 | 0.05 | 0.05 | 0.05 | 0.05 | 0.05 |
| Carbopol ® 934P | 0.4 | 0.4 | 0.4 | 0.4 | 0.4 | 0.4 |
| Polysorbate 80 | 0.05 | 0.05 | 0.05 | 0.05 | 0.05 | 0.05 |
| Mannitol | qs to 300 mOsm/kg | qs to 300 mOsm/kg | qs to 300 mOsm/kg | qs to 300 mOsm/kg | qs to 300 mOsm/kg | qs to 300 mOsm/kg |
| pH | qs to 7.5 | qs to 7.5 | qs to 7.5 | qs to 7.5 | qs to 7.5 | qs to 7.5 |
| Water | qs to 100 | qs to 100 | qs to 100 | qs to 100 | qs to 100 | qs to 100 |

*See Table 1.
**Roughly equivalent to 1.5 wt % of the free base.

Preparation

Compound 3, 12 or 13, and betaxolol or timolol are mixed in 50% of the total water volume component to form an uniform dispersion. Carbopol 934P is slowly added as an aqueous dispersion. The mixture is then homogenized at high speed. The other ingredients are added as aqueous solutions and then water is added to make the final volume. The resultant products, A–F, will be white uniform suspensions.

EXAMPLE 2

The following formulations are typical of aqueous ophthalmic suspensions of the present invention.

| INGREDIENT | AMOUNT (wt %) | | | | | | | |
|---|---|---|---|---|---|---|---|---|
| | G | H | J | K | L | M | N | O |
| Betaxolol HCl | 0.28 | 0.56 | 0.28 | 0.56 | 0.28 | 0.56 | 0.28 | 0.56 |
| Compound 3* | — | — | 1.7** | 1.7** | — | — | — | — |
| Compound 9* | 1.67** | 1.67** | — | — | 1.67** | 1.67** | 1.67** | 1.67** |
| Compound 12* | — | — | — | — | 1.5 | 1.5 | — | — |
| Compound 13* | — | — | — | — | — | — | 1.5 | 1.5 |
| BAC | 0.01 | 0.01 | 0.01 | 0.01 | 0.01 | 0.01 | 0.01 | 0.01 |
| EDTA | 0.05 | 0.05 | 0.05 | 0.05 | 0.05 | 0.05 | 0.05 | 0.05 |
| Amberlite ® IRP-69 | 0.25 | 0.50 | 0.25 | 0.50 | 0.25 | 0.50 | 0.25 | 0.50 |
| Carbopol ® 934P | 0.4 | 2.0 | 0.4 | 2.0 | 0.4 | 2.0 | 0.4 | 2.0 |
| Polysorbate 80 | 0.05 | 0.05 | 0.05 | 0.05 | 0.05 | 0.05 | 0.05 | 0.05 |
| Mannitol | qs to 300 mOsm/kg | qs to 300 mOsm/kg | qs to 300 mOsm/kg | qs to 300 mOsm/kg | qs to 300 mOsm/kg | qs to 300 mOsm/kg | qs to 300 mOsm/kg | qs to 300 mOsm/kg |
| pH | qs to 7.5 | qs to 7.5 | qs to 7.5 | qs to 7.5 | qs to 7.5 | qs to 7.5 | qs to 7.5 | qs to 7.5 |
| Water | qs to 100 | qs to 100 | qs to 100 | qs to 100 | qs to 100 | qs to 100 | qs to 100 | qs to 100 |

*See Table 1.
**Roughly equivalent to 1.5 wt % of the free base.

Preparation

Amberlite, betaxolol and Compound 3, 9, 12 or 13 are mnixed in 50% of the total water volume component to form an uniform dispersion. Carbopol 934P is slowly added as an aqueous dispersion. The mixture is then homogenized at high speed. The other ingredients are added as aqueous solutions and then water is added to make the final volume. The resultant products, G–O, will be white uniform suspensions.

The present invention is also directed to methods of treating and controlling ocular hypertension associated with glaucoma and other ophthalmic diseases and abnormalities. The methods comprise topically applying to the affected eye(s) of the patient a therapeutically effective amount of a composition according to the present invention. The frequency and amount of dosage will be determined by the clinician based on various clinical factors. The methods will typically comprise topical application of one or two drops (or an equivalent amount of a solid or semi-solid dosage form) to the affected eye one to two times per day.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A topical ophthalmic suspension for the treatment of glaucoma and ocular hypertension comprising a beta-blocker and a carbonic anhydrase inhibitor in an ophthalmically acceptable vehicle, wherein the final composition pH is between about 5.0 and 7.8 and wherein the carbonic anhydrase inhibitor is (R)-3,4-dihydro-4-ethylamino-2-(3-mathoxy) propyl-2H-thieno-1,2 thiazine-6-sulfonamide 1,1-dioxide.

2. The composition of claim 1, wherein the final composition concentration of beta-blocker is less than or equal to about 2.0 wt %, and the final composition concentration of carbonic anhydrase inhibitor is less than or equal to about 5 wt %.

3. The composition of claim 2, wherein the final composition concentration of the beta-blocker is between about 0.1 and about 1.0 wt %.

4. The composition of claim 3, wherein the final composition concentration of the beta-blocker is between about 0.25 and about 0.5 wt %.

5. The composition of claim 4, wherein the final composition concentration of the beta-blocker is 0.25 wt %.

6. The composition of claim 2, wherein the final composition concentration of the carbonic anhydrase inhibitor is between about 0.25 and about 3 wt %.

7. The composition of claim 6, wherein the final composition concentration of the carbonic anhydrase inhibitor is about 1.5 wt %.

8. The composition of claim 1, wherein the beta-blocker is selected from the racemic and enantiomeric forms of: betaxolol, timolol, metoprolol, befunolol, falintolol, levobunolol, carteolol, mepindolol, pindolol, bisoprolol, bopindolol, atenolol, arotinolol, acebutolol, nadolol, celiprolol, metipranolol, bevantolol, ICI 118,551, pamatolol, penbutolol, toliprolol, tiprenolol, practolol, procinolol, exaprolol, cicloprolol, carazolol, tazolol, tienoxolol, oxprenolol, propranolol, IPS 339, labetolol, dilevalol, esmolol, bupranolol, bunolol, isoxaprolol, diacetolol, hydroxylevobunolol, carvedilol, and their pharmaceutically acceptable salts.

9. The composition of claim 8, wherein the beta-blocker is selected from the racemic and enantiomeric forms of: betaxolol, timolol, carteolol, levobunolol and hydroxylevobunolol, and their pharmaceutically acceptable salts.

10. The composition of claim 9, wherein the beta-blocker is betaxolol or a pharmaceutically acceptable salt thereof.

11. The composition of claim 9, wherein the beta-blocker is S-timolol or a is pharmaceutically acceptable salt thereof.

12. The composition of claim 1, wherein the beta-blocker is a thiadiazole of formula:

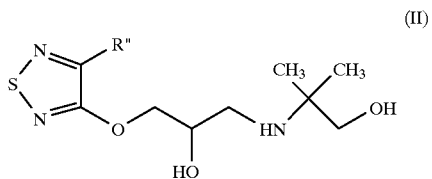

(II)

and optically active isomers and pharmacologically acceptable salts thereof, wherein R" is selected from the group consisting of: hydrogen, halogen, $C_{1-5}$ alkyl, $C_{2-5}$ monoalkenyl, $C_{2-5}$ alkoxy, $C_{3-6}$ cycloalkyl, phenyl, phenalkyl, morpholino, furyl, thienyl and pyrryl.

13. The composition of claim 12, wherein R" is selected from the group consisting of: chlorine, ethyl, allyl, cyclopropyl, ethoxy, phenyl, phenyl-chloromethyl and 2-(cyclopropylmethoxy) ethyl.

14. The composition of claim 1, further comprising an anionic mucomimetic polymer wherein the final composition concentration of the anionic mucomimetic polymer is between about 0.05 and about 8.0 wt %.

15. The composition of claim 14, wherein the final composition concentration of beta-blocker is less than or equal to about 2.0 wt %, and the final composition concentration of carbonic anhydrase inhibitor is less than or equal to about 5 wt %.

16. The composition of claim 15, further comprising a finely-divided drug carrier substrate, wherein the final composition concentration of the finely-divided drug carrier substrate is between about 0.05 and about 10.0 wt %.

17. The composition of claim 14, wherein the beta-blocker is selected from the racemic and enantiomeric forms of: betaxolol, timolol, metoprolol, befunolol, falintolol, levobunolol, carteolol, mepindolol, pindolol, bisoprolol, bopindolol, atenolol, arotinolol, acebutolol, nadolol, celiprolol, metipranolol, bevantolol, ICI 118,551, pamatolol, penbutolol, toliprolol, tiprenolol, practolol, procinolol, exaprolol, cicloprolol, carazolol, tazolol, tienoxolol, oxprenolol, propranolol, IPS 339, labetolol, dilevalol, esmolol, bupranolol, bunolol, isoxaprolol, diacetolol, hydroxylevobunolol, carvedilol, and their pharmaceutically acceptable salts.

18. The composition of claim 14, wherein the beta-blocker is a thiadiazole of formula:

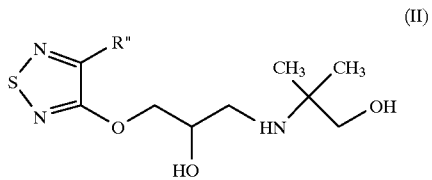

(II)

and optically active isomers and pharmacologically acceptable salts thereof, wherein R" is selected from the group consisting of: hydrogen, halogen, $C_{1-5}$ alkyl, $C_{2-5}$ monoalkenyl, $C_{2-5}$ alkoxy, $C_{3-6}$ cycloalkyl, phenyl, phenalkyl, morpholino, furyl, thienyl and pyrryl.

19. A method for the treatment of glaucoma and ocular hypertension, which comprises, applying to an affected eye a topical ophthalmic suspension comprising a beta-blocker and a carbonic anhydrase inhibitor in an ophthalmically acceptable vehicle, wherein the final composition pH is between about 5.0 and 7.8 and wherein the carbonic anhydrase inhibitor is (R)-3,4-dihydro-4-ethylamino-2-(3-methoxy) propyl-2H-thieno- 1,2 thiazine-6-sulfonamide 1,1-dioxide.

20. The method of claim 19, wherein the beta-blocker is selected from the racemic and enantiomeric forms of: betaxolol, timolol, metoprolol, befunolol, falintolol, levobunolol, carteolol, mepindolol, pindolol, bisoprolol, bopindolol, atenolol, arotinolol, acebutolol, nadolol, celiprolol, metipranolol, bevantolol, ICI 118,551, pamatolol, penbutolol, toliprolol, tiprenolol, practolol, procinolol, exaprolol, to cicloprolol, carazolol, tazolol, tienoxolol, oxprenolol, propranolol, IPS 339, labetolol, dilevalol, esmolol, bupranolol, bunolol, isoxaprolol, diacetolol and hydroxylevobunolol, and their pharmaceutically acceptable salts.

21. The method of claim 20, wherein the beta-blocker is selected from the group consisting of: betaxolol, timolol, carteolol, levobunolol and hydroxylevobunolol, and is their pharmaceutically acceptable salts.

22. The method of claim 19, wherein the beta-blocker is a thiadiazole of formula:

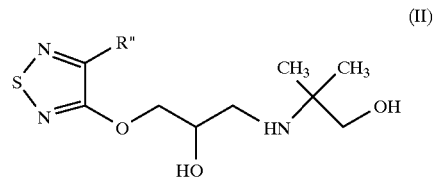

(II)

and optically active isomers and pharmacologically acceptable salts thereof, wherein R" is selected from the group consisting of: hydrogen, halogen, $C_{1-5}$ alkyl, $C_{2-5}$ monoalkenyl, $C_{2-5}$ alkoxy, $C_{3-6}$ cycloalkyl, phenyl, phenalkyl, morpholino, furyl, thienyl and pyrryl.

23. The method of claim 22, wherein R" is selected from the group consisting of: chlorine, ethyl, allyl, cyclopropyl, ethoxy, phenyl, phenyl-chloromethyl and 2-(cyclopropylmethoxy)ethyl.

* * * * *